United States Patent [19]

Drell et al.

[11] 4,105,794

[45] Aug. 8, 1978

[54] PROCESS OF MITIGATING CHOLELITHIASIS

[75] Inventors: William Drell; John Kingsley Pollard, Jr., both of La Jolla, Calif.

[73] Assignee: Calbiochem-Behring Corp., La Jolla, Calif.

[21] Appl. No.: 821,804

[22] Filed: Aug. 4, 1977

[51] Int. Cl.$^2$ ............... A61K 31/205; A61K 31/535; A61K 31/495

[52] U.S. Cl. .................................. 424/317; 424/250; 424/248.4

[58] Field of Search ........................................ 424/317

[56] References Cited

U.S. PATENT DOCUMENTS 3,629,449  12/1971  Siddigi et al. ..................... 424/317

*Primary Examiner*—Donald B. Moyer
*Attorney, Agent, or Firm*—Natalie Jensen

[57] ABSTRACT

Therapeutic composition useful for mitigating cholelithiasis in humans comprising 3-hydroxy-3-methylglutaric acid, or a pharmaceutically acceptable salt thereof, and a pharmaceutically acceptable non-toxic carrier.

4 Claims, No Drawings

PROCESS OF MITIGATING CHOLELITHIASIS

The present invention relates to a therapeutic composition and method for mitigating cholelithiasis in humans. More particularly, the present invention relates to a therapeutic composition containing 3-hydroxy-3-methylglutaric acid, or a pharmaceutically acceptable salt thereof, and to methods utilizing these compounds as the essential ingredient in the mitigation of cholelithiasis.

Cholelithiasis, the medical term denoting the presence or formation of gallstones, is responsible for over 475,000 operations in the United States annually. The disease affects three times as many women as men with the differences beginning at puberty and declining somewhat in later years.

Although gallstones can form anywhere in the bilary tract, it is believed that most of them form in the gallbladder. In Western cultures cholesterol is the principal ingredient of more than 90 percent of the gallstones. It has been demonstrated that cholesterol gallstone formation in man is associated with abnormalities in the relative concentrations of the major bilary lipids, i.e., cholesterol, bile acid salts, and phospholipids. Moreover, it is now recognized generally that cholesterol gallstones occur in gallbladder bile that contains more cholesterol than can be solubilized by the available bile acid salts and phospholipids.

Traditional treatment of acute cholelithiasis has been surgical removal of the gallbladder, entailing great financial and emotional cost for the affected subjects. In 1975 the sixth most common cause for hospitalization was cholecystectomy, i.e., surgical removal of the gallbladder.

Recently it has been reported that preliminary experiments show that chenodeoxycholate (one of the primary bile acids) partially or completely dissolves gallstones in a majority of patients tested. Of concern, however, is the possibility that lithocholate, a secondary bile acid formed from chenodeoxycholate, might damage the liver or that prolonged consumption of chenodeoxycholate might interfere with the endogenous cholesterol degredation (Way, L. W., "Diseases of the Gallbladder and Bile Ducts," p. 1310, *Textbook of Medicine*, edited by Beeson and McDermott, 14th edition, W. B. Saunders, Philadelphia, 1975). In view of the aforementioned concern, it is obvious that additional agents are needed if chemotherapeutic treatment of cholelithiasis is to replace surgery.

It has now been found that 3-hydroxy-3-methylglutaric acid and pharmaceutically acceptable salts thereof are effective agents in the mitigation of cholelithiasis. This discovery was completely unexpected based on the stated utility of the acid in reducing serum cholesterol and triglyceride levels (U.S. Pat. No. 3,629,449) since recent reports indicate that some hypolipidemic agents increase the incidence of cholelithiasis.

Accordingly, the present invention in a first aspect is directed to a therapeutic composition for mitigating cholelithiasis in human, which composition comprises an effective amount of 3-hydroxy-3-methylglutaric acid, or pharmaceutically acceptable salt thereof, and a pharmaceutically acceptable non-toxic carrier.

The present invention in a second aspect is directed to a method for mitigating cholelithiasis in humans, which method comprises administering an effective amount of 3-hydroxy-3-methylglutaric acid, or a pharmaceutically acceptable salt thereof; or a therapeutic composition containing said acid or salt as the essential ingredient.

The pharmaceutical carriers used in the preparation of the therapeutic compositions of the instant invention can be either solid materials or liquids in which the acid or salt thereof is dissolved, dispersed or suspended. Thus, the compositions can take the form of tablets, capsules, powders, solutions, suspensions, emulsions, syrups, elixers and the like. Pharmaceutically acceptable non-toxic carriers or excipients normally employed for solid formulations include, for example, starch, lactose, glucose, sucrose, cellulose, gelatin, talc, silica gel, magnesium stearate, sodium stearate, glycerol monostearate, and the like. Pharmaceutically acceptable non-toxic carriers normally employed for liquid formulations include, for example, water, saline solution, aqueous dextrose, glycerol, propylene glycol and the like. The therapeutic compositions of the instant invention may be subjected to conventional expedients, such as sterilization, and can contain conventional pharmaceutical excipients, such as preservatives, stabilizing agents, emulsifying agents and buffers. The compositions may also contain other therapeutically active medicaments.

In practicing the instant invention, 3-hydroxy-3-methylglutaric acid, or a pharmaceutically acceptable salt thereof, or a therapeutic composition containing said acid or salt, is administered by conventional methods, i.e., orally (preferred) or parenterally. Parenteral administration includes intramuscular as well as subcutaneous and intravenous injection. In general, for oral and parenteral administration, it is expedient to administer the active ingredient, e.g., 3-hydroxy-3-methylglutaric acid, or a pharmaceutically acceptable salt, in amounts of between about 10 to 100 mg/kg. body weight per day (preferably between about 20 to 50 mg/kg. body weight per day in dividend portions, e.g., in three individual doses, in order to achieve effective results. The exact regimen for administration of 3-hydroxy-3-methylglutaric acid, pharmaceutically acceptable salts thereof, or therapeutic compositions containing same, will necessarily be dependent upon the needs of an individual subject being treated. In any event, the amount of medicament administered will be in an amount effective for the mitigation of cholelithiasis. The ratio of acid or salt to carrier will vary depending upon the concentration of medicament desired in the final unit dosage form. In general, the concentration of medicament will be in the range of 25 to 90 weight percent of the therapeutic composition.

The term pharmaceutically acceptable salts, as used hereinabove and below, refers to those salts of 3-hydroxy-3-methylglutaric acid which do not adversely affect the pharmaceutical properties of the acid and which are prepared by treating 3-hydroxy-3-methylglutaric acid with a pharmaceutically acceptable base. Representative salts derived from such bases include, but are not limited to, the sodium, potassium, calcium, lithium, magnesium, ferric, aluminum, ammonium, N-methyl-glucamine, glucamine, morpholine, and piperazine salts. The pharmaceutically acceptable salts can be prepared according to procedures well known in the art, for example, by simply treating the free acid with a pharmaceutically acceptable inorganic or organic base affording the desired cation.

The term mitigating cholelithiasis, as used hereinabove and below, refers to reducing or preventing the formation of gallstones and/or lithogenic bile and partially or completely dissolving existing gallstones in subjects where such treatment is indicated.

The following specific description is given to enable those skilled in the art to more clearly understand the present invention. It should not be considered as a limitation on the scope of the invention but merely as an illustrative and representative description thereof.

EXAMPLE 1

The following example illustrates a representative formulation containing 3-hydroxy-3-methylglutaric acid which formulation may be used for mitigating cholelithiasis.

| A. Oral Formulation Ingredient | parts by weight |
|---|---|
| 3-hydroxy-3-methylglutaric acid | 250 |
| Microcrystalline cellulose | 200 |
| Tablet lubricant* | 4 |

*Tablet lubricant, i.e., hydrogenated vegetable oil such as that obtained from Capitol City Products, Columbus, Ohio under the trademark Sterotex.

3-Hydroxy-3-methylglutaric acid (250 parts) and 75 parts of microcrystalline cellulose are blended in a Colton blender for approximately 20 minutes. The blended mixture is then granulated using ethanol as the solvent. The wet granulation is passed through a #4 screen and dried at 45° C for approximately 16 hours.

The above obtained dried granules are passed through a #12 screen and combined with about 99 parts of microcrystalline cellulose in a Waring blender.

Sterotex (4 parts) and about 26 parts microcrystalline cellulose are hand blended for approximately 3 minutes. Thereafter the mixture is passed through a #30 screen and added to the mixture described in the previous paragraph. The combined ingredients are blended for 30 minutes and the formulation is then formed into tablets (containing 250 mg. of 3-hydroxy-3-methylglutaric acid) with an appropriate tabletting machine.

EXAMPLE 2

The following example illustrates the action of 3-hydroxy-3-methylglutaric acid in mitigating cholelithiasis in hamsters fed a lithogenic (i.e., gallstone inducing) diet.

Syrian hamsters approximately 3 months old were fed ad libitum a diet consisting of:
  73.8% Dextrose
  20.0% Casein
  0.2% Choline chloride
  1.0% Vitamin Mix*
  5.0% Salt Mix U.S.P. XIV**

*Vitamin Mix (gm/kgm diet): p-aminobenzoic acid (0.11); vitamin C (1.017); Biotin (0.0004); Ca pantothenate (0.066); choline citrate (3.715); folic acid (0.002); inositol (0.11); vitamin K (0.05); nicotinic acid (0.009); pyridoxine HCl (0.022); riboflavin (0.022); vitamin A acetate, 500,000 IU/gm (0.004); vitamin E acetate, 250 IU/gm (0.485).
**Salt Mix USP XIV (%): $Al_2(SO_4)_3.24 H_2O$ (0.009); $CaHPO_4.2 H_2O$ (11.28); $CaCO_3$ (6.86); $Ca_3(C_6H_5O_7)_2.4 H_2O$ (30.83); $CuSO_4$ (0.008); $Fe(NH_4)(C_6H_5O_7)_2$ (1.526); $MgCO_3$ (3.520); $MgSO_4$ (3.83); $MnSO_4$ (0.02) KCL (12.47); KI (0.004); $KH_2PO_4$ (21.88); NaCl (7.71); NaF (0.05).

After 30 days on the diet, 19 animals were sacrificed and autopsied to establish a gallstone base line. The incidence of gallstones in this group was 68%; the incidence of gallstones and lithogenic bile (i.e., bile supersaturated with cholesterol) was 89%.

The remaining animals were then separated into six groups, each group being fed one of the following diets: Purina lab chow, Purina lab chow containing 0.05% 3-hydroxy-3-methylglutaric acid, the lithogenic diet described in the previous paragraph, or the lithogenic diet containing 0.05% or 0.2% 3-hydroxy-3-methylglutaric acid. 3-Hydroxy-3-methylglutaric acid was added to the diet at the expense of dextrose.

After 60 days, and then after 90 days on the aforementioned diets, animals from each group were sacrificed and autopsied and gallbladders and bile ducts were examined for visible stones. In addition, bile was examined for signs of lithogenicity.

The results of the above described study are shown in the following table.

Effect of Various Dietary Regimens on Gallstone Formation and Lithogenic Bile

| Regimen* | Incidence of Visible Stones | | Incidence of Visible Stones and Lithogenic Bile | |
|---|---|---|---|---|
| | 60 days | 90 days | 60 days | 90 days |
| C | 4/8 | 8/21 | 8/8 | 17/21 |
| C + 0.05% HMG | 4/8 | 4/18 | 8/8 | 15/18 |
| L | 8/11 | No survivors | 10/11 | No survivors |
| L + 0.05% HMG | 4/8 | 9/17 | 4/8 | 16/17 |
| L + 0.20% HMG | 3/8 | 6/13 | 6/8 | 10/13 |

*C, Purina lab chow; L, lithogenic diet; HMG, 3-hydroxy-3-methyl-glutaric acid.

In 11 animals whose gallbladders were examined after maintenance on the lithogenic diet for 60 days, the incidence of gallstones was 73%. There were no survivors in the group destined for a 90 day regimen on the lithogenic diet. The addition of 0.2% 3-hydroxy-3-methylglutaric acid to the lithogenic diet reduced the incidence of gallstones to 38% in animals maintained on the diet for 60 days and to 46% in animals maintained on the diet for 90 days. Moreover, the incidence of visible stones and lithogenic bile in animals maintained on the lithogenic diet for 60 days was reduced from 91% to 75% when 0.2% 3-hydroxy-3-methylglutaric acid was added to the diet. The incidence of visible stones and lithogenic bile in animals maintained for 90 days on the lithogenic diet containing 0.2% 3-hydroxy-3-methylglutaric acid was 77%.

It is evident from the above data that the administration of 3-hydroxy-3-methylglutaric acid to hamsters fed a lithogenic diet reduces the incidence of gallstones and lithogenic bile and significantly increases the survival time of the animals.

The invention being thus described, it will be obvious that the same may be varied in many ways. Such variations are not to be regarded as a departure from the spirit and scope of the invention, and all such modifications are to be included within the scope of the following claims.

What is claimed is:

1. A method of mitigating cholelithiasis in humans comprising administering a therapeutically effective amount of 3-hydroxy-3-methylglutaric acid or a pharmaceutically acceptable salt thereof.

2. A method according to claim 1 wherein about 10 to 100 mg./kg. of body weight of 3-hydroxy-3-methylglutaric acid, or a pharmaceutically acceptable salt thereof, is administered.

3. A method according to claim 2 wherein 3-hydroxy-3-methylglutaric acid, or a pharmaceutically acceptable salt thereof, is administered in a pharmaceutically acceptable, non-toxic carrier.

4. A method according to claim 3 wherein administration is oral.

* * * * *